United States Patent [19]

Strahorn

[11] 4,152,528
[45] May 1, 1979

[54] PROCESS FOR EXTRACTING PHENOL FROM PHENOL-WATER MIXTURES

[75] Inventor: David F. Strahorn, Oakland, Calif.

[73] Assignee: Chevron Research Company, San Francisco, Calif.

[21] Appl. No.: 788,104

[22] Filed: Apr. 15, 1977

[51] Int. Cl.$^2$ ............................................. C07C 37/34
[52] U.S. Cl. ....................................... 568/749; 568/761
[58] Field of Search ........... 260/621 A, 621 B, 627 R, 260/624 A, 626 R, 627; 568/749, 761

[56] References Cited

U.S. PATENT DOCUMENTS

| | | | |
|---|---|---|---|
| 2,807,654 | 9/1959 | Grimmett | 260/627 R |
| 2,928,882 | 3/1960 | Hall | 260/627 R |
| 3,155,734 | 11/1964 | Merkel | 260/621 R |

OTHER PUBLICATIONS

Zlatin et al. Chem. Abs. vol. 59, 13683e (1963).
Aunicky Chem. Abs. vol. 63, 393e (1965).
Ivonon et al. Chem. Abs. vol. 54, 15905 (1960).

Primary Examiner—Werren B. Lone
Attorney, Agent, or Firm—D. A. Newell; R. H. Davies; W. D. Reese

[57] ABSTRACT

A process is provided for extracting phenol from phenol-water mixtures using a hydrocarbon-extracting medium having an improved extraction coefficient. The extracting medium comprises a mixture of a hydrocarbon component containing at least a substantial amount of an aromatic hydrocarbon for example benzene, and a ketone component, for example 2-butanone.

6 Claims, 1 Drawing Figure

PARTITION COEFFICIENTS$^{(1)}$ FOR
BENZENE-2-BUTANONE (B-2-B) MIXTURES
AT 22° C

WT. % 2-BUTANONE (1) $K = \dfrac{\text{WT. \% PHENOL IN B-2-B MIXTURES}}{\text{WT. \% PHENOL IN WATER PHASE}}$

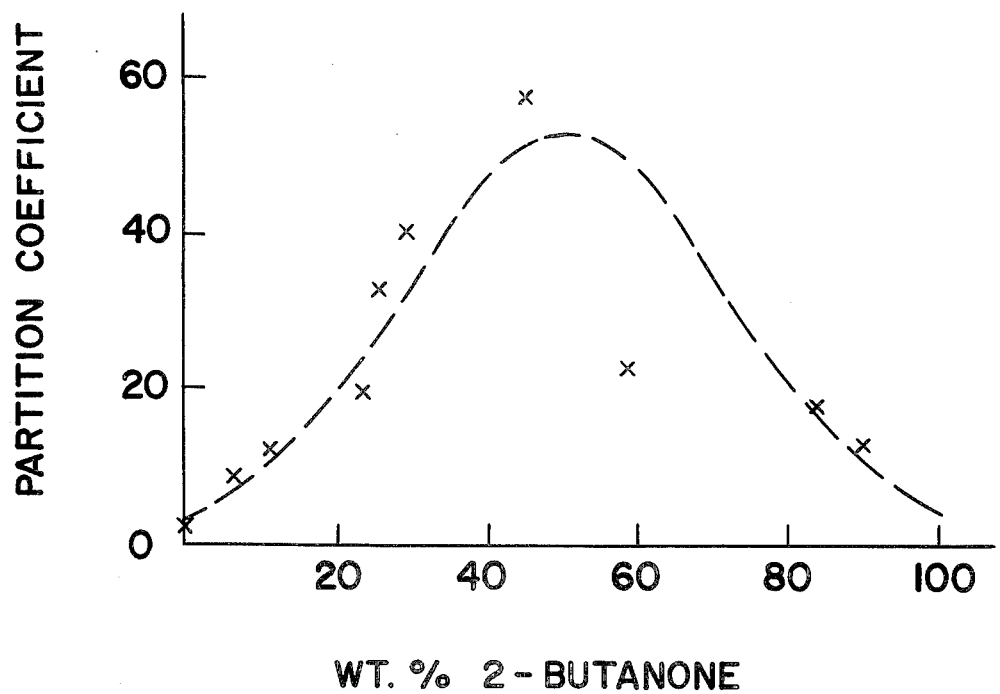

PROCESS FOR EXTRACTING PHENOL FROM PHENOL-WATER MIXTURES

BACKGROUND OF THE INVENTION

This invention relates to an improved process for extracting phenol from a phenol-water mixture. More particularly, it relates to carrying out the aforementioned extracting using an extracting medium comprising an aromatic hydrocarbon component and a ketone component.

The recovery of phenol from aqueous phenolic mixtures using benzene as the extracting solvent, for example from (1) tar water, (2) aqueous phenolic wastes, and (3) aqueous coke-oven wastes, is described in articles by (i) B. I. Ivanov et al., (ii) L. I. Zlatin et al. and (iii) Zd Aunicky. These articles are cited in the Chemical Abstracts of the American Chemical Society at Vol. 54:15905i, Vol. 59:13683e and Vol. 63:393e, respectively. However, the phenol extraction coefficient for the benzene-water system is small, for example it is less than 5. The lower the coefficient, of course, the larger is the number of extraction stages which must be used for an effective recovery of phenol in an extracting process and the larger is the amount of solvent which must be processed. Accordingly, there is a need for a phenol extracting medium having an improved extraction coefficient.

It is an object of this invention to provide an extracting medium having an improved extraction coefficient. A further object is to provide an improved process for recovering phenol from water-phenol mixtures using such a medium.

SUMMARY OF THE INVENTION

In the process for extracting phenol from a liquid phase comprising phenol and water by contacting said phase under liquid-liquid extracting conditions with an extracting medium thereby producing an aqueous raffinate phase and an organic extract phase, an improvement is provided comprising: (1) using as said medium a liquid mixture containing a hydrocarbon component, and a ketone component, said hydrocarbon component containing (a) at least about 25 weight percent of at least one aromatic hydrocarbon selected from the group consisting of (i) benzene, and (ii) lower alkyl-substituted benzenes containing less than 4 alkyl substituent groups, and (b) a remainder, if any, selected from the group consisting of non-aromatic hydrocarbon solvents; said ketone component being at least one ketone selected from the group consisting of ketones composed of carbon, hydrogen and oxygen and having a carbon atom content in the range from 3 to about 7; and said medium containing at least sufficient of said ketone to produce, in extracting phenol from water, a phenol extraction coefficient for said medium which is at least a factor of about 2 greater than the phenol extraction coefficient for said hydrocarbon component; and (2) separating said raffinate and extract phases.

DESCRIPTION OF THE DRAWING

The FIGURE is a curve showing the enhancement of the phenol extraction coefficient resulting from the addition of 2-butanone to the benzene in a benzene-water system.

EMBODIMENT

In a preferred embodiment phenol is recovered from an aqueous phenolic process stream produced in refining a petroleum stock. A typical such stream is a steam-stripping condensate containing, in parts by weight, about 1 part of phenol and about 99 parts of water. In the embodiment, this stream is contacted with recycled extracting medium which is a 50/50 (volume) mixture of benzene and 2-butanone containing about 1000 ppmw of phenol. The contacting is carried out in an ordinary countercurrent extracting column at a volume ratio of extracting medium to aqueous phenol of about 0.05. The resulting aqueous raffinate phase contains less than 100 ppmw of phenol. In order to achieve a comparable extraction of the phenol from the water using benzene alone as the extracting medium, it would be necessary to use per volume of feed a volume of benzene having less than 300 ppmw of phenol which is at least a factor of about 10 greater than the volume of the 50/50 benzene-ketone extracting medium.

By "liquid-liquid extracting conditions" as used herein is meant by definition efficient contacting of at least two liquid phases carried out under conditions of temperature and pressure at least sufficient to maintain said liquid phases.

Liquid-liquid extracting conditions are known and used in the extracting art, and such are contemplated for use in the usual way herein. Representative conditions, methods and equipment suitable for use in liquid-liquid extracting for directly contacting separable liquid phases for the purpose of causing transfer of a dissolved substance, for example, phenol as herein, are described in Perry's Chemical Engineers' Handbook, 4th Ed., R. H. Perry, C. H. Chilton and S. D. Kirkpatrick, co-editors, McGraw-Hill Book Company, New York, Sections 21-10 to 21-34. Other leading references are also cited in the above Handbook.

EXAMPLES

In a series of runs which were carried out under ambient conditions, that is, at a temperature of about 22° C. and a pressure of 1 atmosphere, the phenol partition coefficients for water and a series of ketone-modified hydrocarbon extracting phases were determined. The extracting phases used in these examples were benzene and a benzene solution containing a range of 2-butanone contents. The results from these runs are shown in the FIGURE. These results illustrate that while benzene or 2-butanone individually exhibit phenol partition coefficients of a relatively low order, for example of less than about 3 or 5, mixtures of benzene and 2-butanone exhibit, in the partition of phenol between water and the organic extracting medium, partition coefficients which are receptional. From the FIGURE it is notable that the addition of but a minor amount of 2-butanone, for example as little as 10 weight percent, to benzene about doubles the partition coefficient. The coefficient for a 50/50 mixture, relative to that for benzene alone, is larger by about a factor of 20!

Process Parameters

(A) Extracting Medium

The hydrocarbon solvents suitable for use herein may vary widely and, in general, must exhibit an appreciable aromatic character, for example as exhibited by a hydrocarbon mixture having an aromatic hydrocarbon content of at least about 25 volume percent, preferably in the range of from about 40 to 65. As may be noted from the FIGURE, excellent results, in terms of an improved phenol partition coefficient, are achieved when the hydrocarbon components consist essentially of aromatic hydrocarbons. However, for practical reasons, including (1) cost and/or (2) concurrent coextraction of non-aromatic hydrocarbons from the phenolic aqueous phase, a diluted aromatic hydrocarbon extracting phase will frequently be that of choice for use herein, especially where the process is being carried out in a continuous mode. Where the hydrocarbon component contains a non-aromatic diluent, the latter may be any known normally liquid non-aromatic hydrocarbon solvent or fraction thereof. Representative diluents include paraffinic and olefinic petroleum fractions, hexane, hexene, cyclohexane, cyclohexene, heptane, heptene, and the like hydrocarbon solvents, and paraffinic and olefinic components and fractions thereof which are normally present in substantially aromatic product streams ordinarily recovered in a petroleum refinery.

The aromatic hydrocarbons comprising benzene and alkyl-substituted benzenes and mixtures thereof are preferred for use as the extracting medium or as components thereof in the present process. Preferably, the aromatic component of the extracting medium contains at least one hydrocarbon selected from the group consisting of benzene and lower alkyl (alkyl groups containing less than 4 carbon atoms), substituted benzenes containing less than 4 alkyl substituent groups. Representative aromatic components include benzene, toluene, the xylenes, ethylbenzene, cumene and mixtures thereof. Benzene and toluene are preferred.

(B) Ketone Component

The ketone component of the extracting medium may be 2-butanone, 2-pentanone, 3-pentanone, acetone and the like ketones and mixtures thereof, that is, there may be at least one ketone selected from the group consisting of ketones composed of carbon, hydrogen and oxygen and having a carbon atom content in the range from 3 to about 7. In addition to the aforenamed ketones, representative ketones suitable for use herein include cyclohexanone, cyclopentanone, methyl-substituted cyclohexanone or cyclopentanone, isopropylmethyl, ethyl isopropyl and the like acyclic ketones. 2-butanone is a preferred ketone component for use herein.

The amount of ketone desirably present in the extracting medium varies depending upon a number of factors, including the kind and amount of aromatic hydrocarbon in the hydrocarbon component, the particular ketone component employed and the temperature at which the extracting is carried out. In general, an improved extracting medium is obtained when this medium contains an amount of ketone in the range from about 5 to 90 weight percent. Preferably the medium contains by weight an amount of the ketone in the range from about 20 to 80%, and more preferably 40 to 65%.

(C) Temperature and Pressure

The temperature and pressure combinations suitable for use herein are in general those sufficient to maintain the liquid phases herein in the liquid phase. Preferably the contacting, in order to avoid use of costly pressure equipment, is carried out at atmospheric pressure. Suitable temperatures in this case will, of course, be below the boiling point of the lowest-boiling component in the extracting system. Preferred contacting temperatures are in the range from about 10° C. to 50° C. and most preferably about the ambient temperature.

(D) Extracting Medium to Phenolic Water Volume Ratio

The extracting medium to phenolic water volume ratio may vary widely, depending upon the particular extracting medium being employed and the phenol content of the phenolic water phase. At least sufficient of the extracting medium must be employed in the contacting to result in the required aqueous raffinate phase and an organic extract phase, that is, sufficient to satisfy ordinary liquid-liquid extracting conditions. In general, satisfactory volumetric operating ratios are in the range from about 0.05 to 15 and preferably 0.1 to 1.

Apparatus

Any suitable form of apparatus may be used. In general, the various means customarily employed in extraction processes to increase the contact area between the two separate liquid phases can be employed. Thus the apparatus used in the present process can comprise a single extraction zone or multiple extraction zones equipped with (a) shed rows or stationary devices to facilitate contacting; (b) orifice mixers; or (c) effective stirring devices such as mechanical agitators, jets of restricted internal diameter, turbomixers, and the like.

Apparatus suitable in the batch- or continuous-type manner, the latter being preferred, may be employed. A continuous countercurrent operation employing a liquid-liquid contacting tower is a preferred mode.

Reasonable variation and modification are possible within the scope of the disclosure, the drawing and the appended claims to the invention, the essence of which is that there has been provided a method for improving the extraction of phenol from a phenol-water mixture by increasing the phenol partition coefficient of a hydrocarbon extracting medium by adding a suitable ketone to the medium.

What is claimed is:

1. In the process for extracting phenol from a liquid phase comprising phenol and water by extracting said phase under conventional liquid-liquid extracting conditions with an extracting medium thereby producing an aqueous raffinate phase and an organic extract phase, said conditions including a temperature of 10°–50° C., and pressure at least sufficient to maintain said liquid phases, the improvement comprising: (1) using as said medium a liquid mixture containing a hydrocarbon component, and a ketone component, said hydrocarbon component containing at least 25 weight percent of aromatic hydrocarbon being selected from the group consisting of benzene and alkyl-substituted benzenes containing less than 4 alkyl substituent groups, said alkyl groups containing less than 4 carbon atoms; said ketone component being at least one aliphatic ketone selected from the group consisting of aliphatic ketones composed of carbon, hydrogen and oxygen and having a carbon atom content in the range from 3 to 7; said medium containing an amount of said ketone, in the range 20–80 weight percent, sufficient to produce, in extracting phenol from water, a phenol extraction coefficient for said medium which is at least a factor of about 2 greater than the phenol extraction coefficient for said hydrocarbon component; and (2) said conditions including using a volume ratio of extracting medium to phenolic water in the range of from about 0.05-15 to 1, respectively.

2. A process as in claim 1 wherein:
   (a) said aromatic hydrocarbon group is benzene and toluene;
   (b) said hydrocarbon component contains an amount by volume of said aromatic hydrocarbon in the range of from about 40 to 65 percent.

3. A process as in claim 2 wherein said ketone is 2-butanone.

4. A process as in claim 1 wherein said volume ratio is in the range of from about 0.1-1 to 1, respectively.

5. A process as in claim 2 wherein said amount of ketone is in the range of from about 40 to 65 weight percent.

6. A process as in claim 1 wherein:
   (a) said contacting medium is about a 50/50 (volume) mixture of benzene and 2-butanone;
   (b) said contacting is carried out using an extracting medium to phenolic water volume ratio of about 3; and
   (c) said raffinate per million parts by weight has a phenol content which is less than about 1000.

* * * * *